United States Patent
Bonutti

(10) Patent No.: US 6,171,236 B1
(45) Date of Patent: *Jan. 9, 2001

(54) METHOD OF RETRACTING SOFT TISSUE FROM A BONE

(75) Inventor: Peter Mark Bonutti, Effingham, IL (US)

(73) Assignee: General Surgical Innovations, Inc., Norwalk, CT (US)

( * ) Notice: Under 35 U.S.C. 154(b), the term of this patent shall be extended for 0 days.

This patent is subject to a terminal disclaimer.

(21) Appl. No.: 09/299,770

(22) Filed: Apr. 26, 1999

Related U.S. Application Data

(63) Continuation of application No. 08/593,299, filed on Jan. 29, 1996, now Pat. No. 6,017,305, which is a continuation of application No. 08/419,851, filed on Apr. 10, 1995, now abandoned, which is a continuation of application No. 08/216,097, filed on Mar. 22, 1994, now abandoned, which is a continuation of application No. 08/054,416, filed on Apr. 28, 1993, now abandoned, which is a division of application No. 07/487,645, filed on Mar. 2, 1990, now Pat. No. 5,331,975.

(51) Int. Cl.[7] .................................................. A61B 1/32
(52) U.S. Cl. ........................................ 600/207; 606/192
(58) Field of Search ........................... 604/174, 178, 604/101; 600/207, 116, 115; 606/90, 192

(56) References Cited

U.S. PATENT DOCUMENTS

| 3,417,745 | 12/1968 | Sheldon | 128/6 |
|---|---|---|---|
| 3,774,596 | 11/1973 | Cook | 606/192 |
| 3,863,639 | 2/1975 | Kleaveland | 128/303 |
| 3,882,852 | 5/1975 | Sinnreich | 128/4 |
| 4,312,353 | 1/1982 | Shahbabian | 600/207 |
| 4,630,609 | 12/1986 | Chin | 128/344 |
| 4,779,611 | 10/1988 | Grooters et al. | 600/116 |
| 4,798,205 | * 1/1989 | Bonomo et al. | 606/192 |
| 5,163,949 | 11/1992 | Bonutti | 606/192 |
| 5,183,464 | 2/1993 | Dubrul et al. | 128/3 |
| 5,197,971 | 3/1993 | Bonutti | 606/192 |
| 5,514,091 | 5/1996 | Yoon | 600/207 |
| 5,514,153 | 5/1996 | Bonutti | 606/190 |

OTHER PUBLICATIONS

Eduardo Sanchez de Badajoz et al, Uretropexia Laparoscópica, Arch. Esp. de Urol, 46.7 (642–644), 1993.

Eduardo Sanchez de Badajoz Chamorro et al., Anclaje cervical endoscópico. Nuevo tratamiento para la incontinencia de esfuerzo, Arch Esp. de Urol., 41, 2 (127–130), 1988.

* cited by examiner

Primary Examiner—Michael H. Thaler

(57) ABSTRACT

A fluid operated retractor for use in surgery. The retractor has a portion that is expandable upon the introduction of fluid under pressure. The expandable portion is made of a material strong enough, and is inflated to enough pressure, to spread adjoining tissues within the body. The retractor is especially useful in fiber optic surgery because it can be inserted percutaneously through a small opening then expanded to a much larger dimension when in the desired location, to retract tissue from within. The retractor may be used to spread a joint such as a knee joint or a shoulder joint, or may be used to separate tissue planes generally, to improve visualization and create a working space for the surgeon.

15 Claims, 11 Drawing Sheets

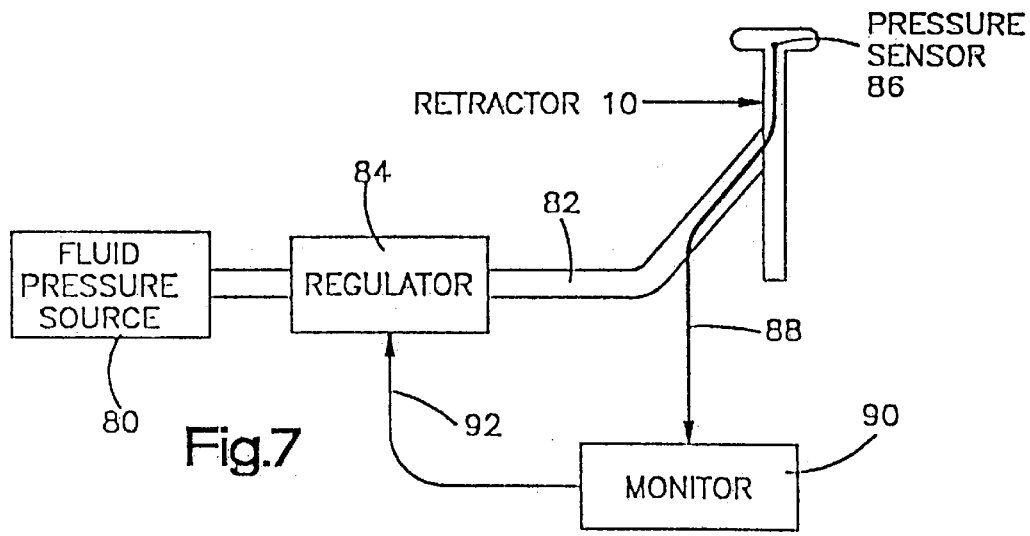
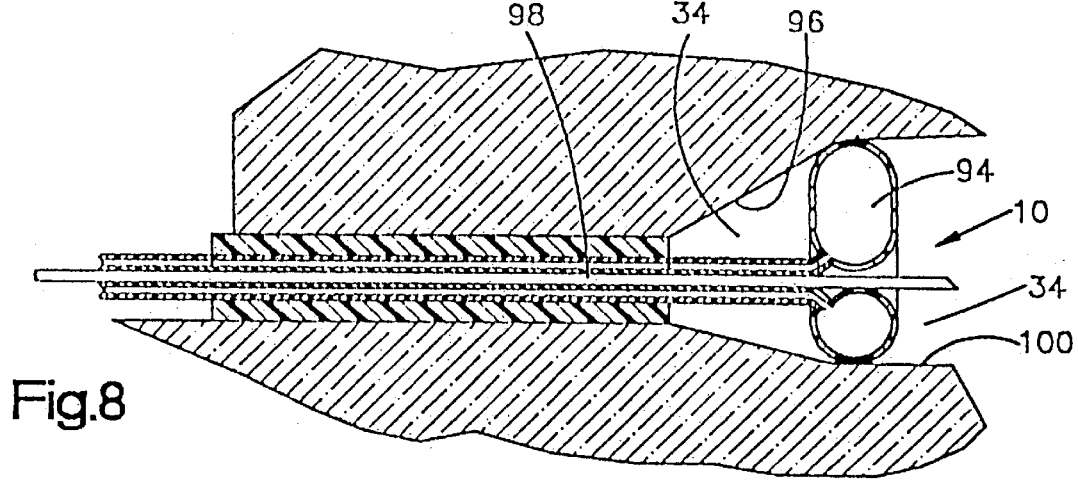
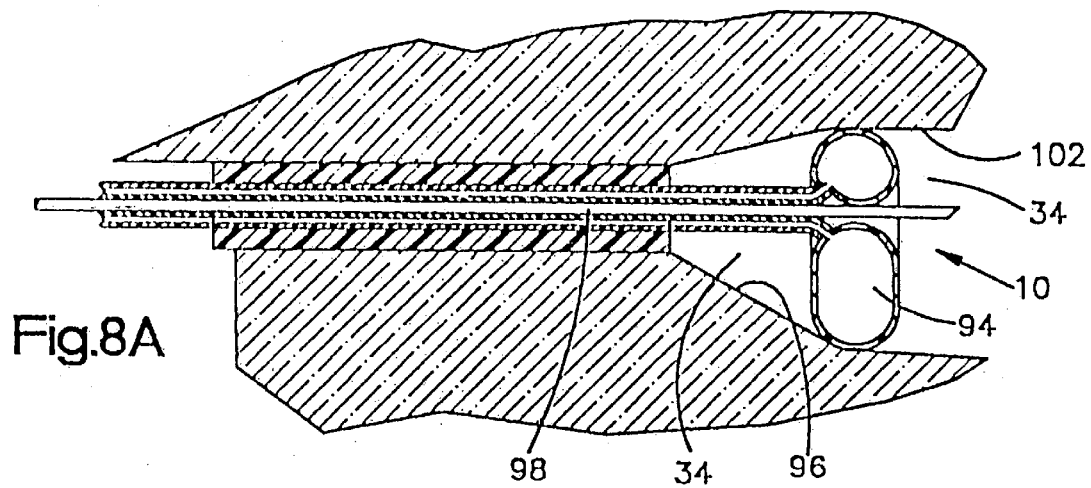

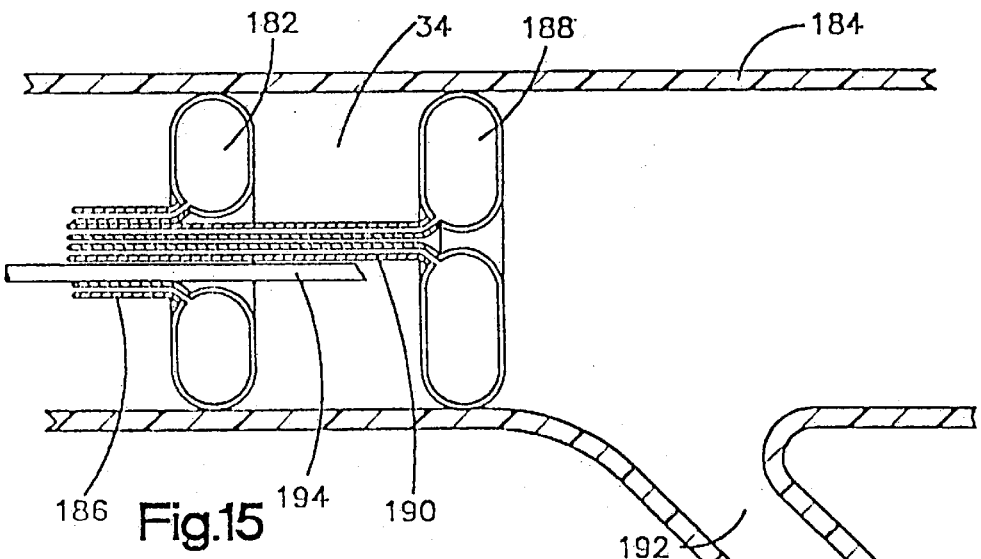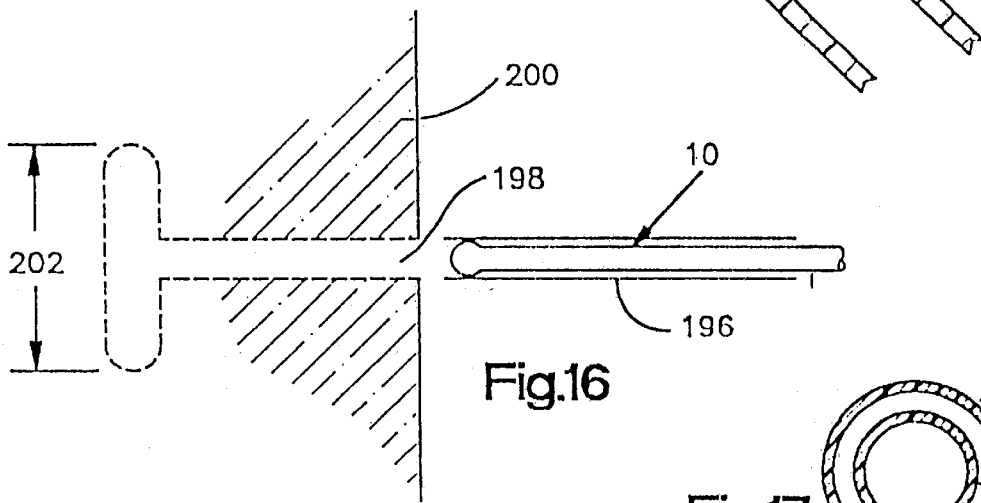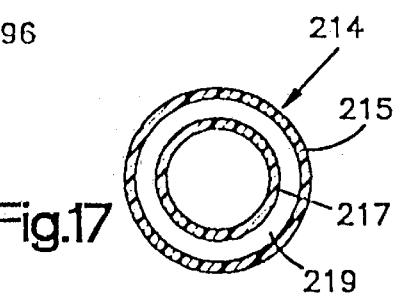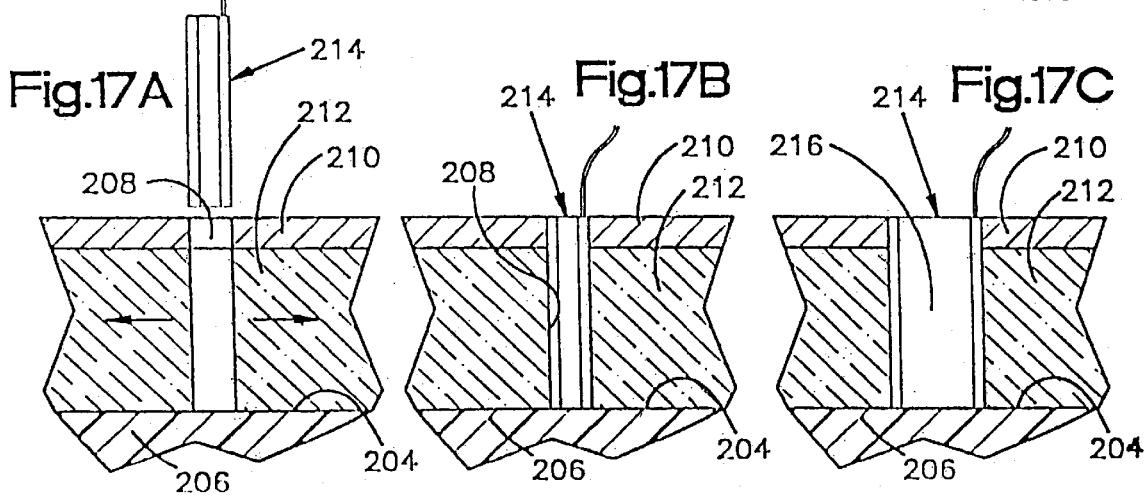

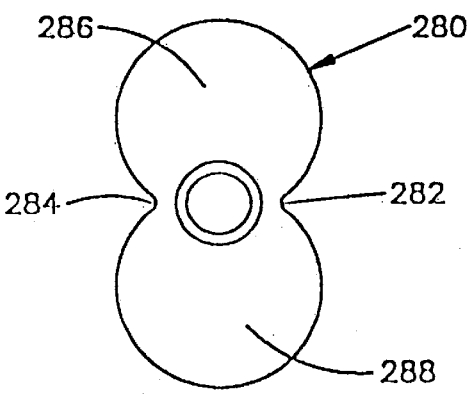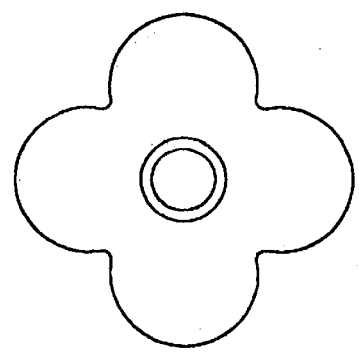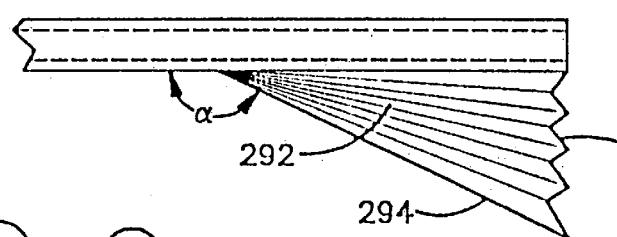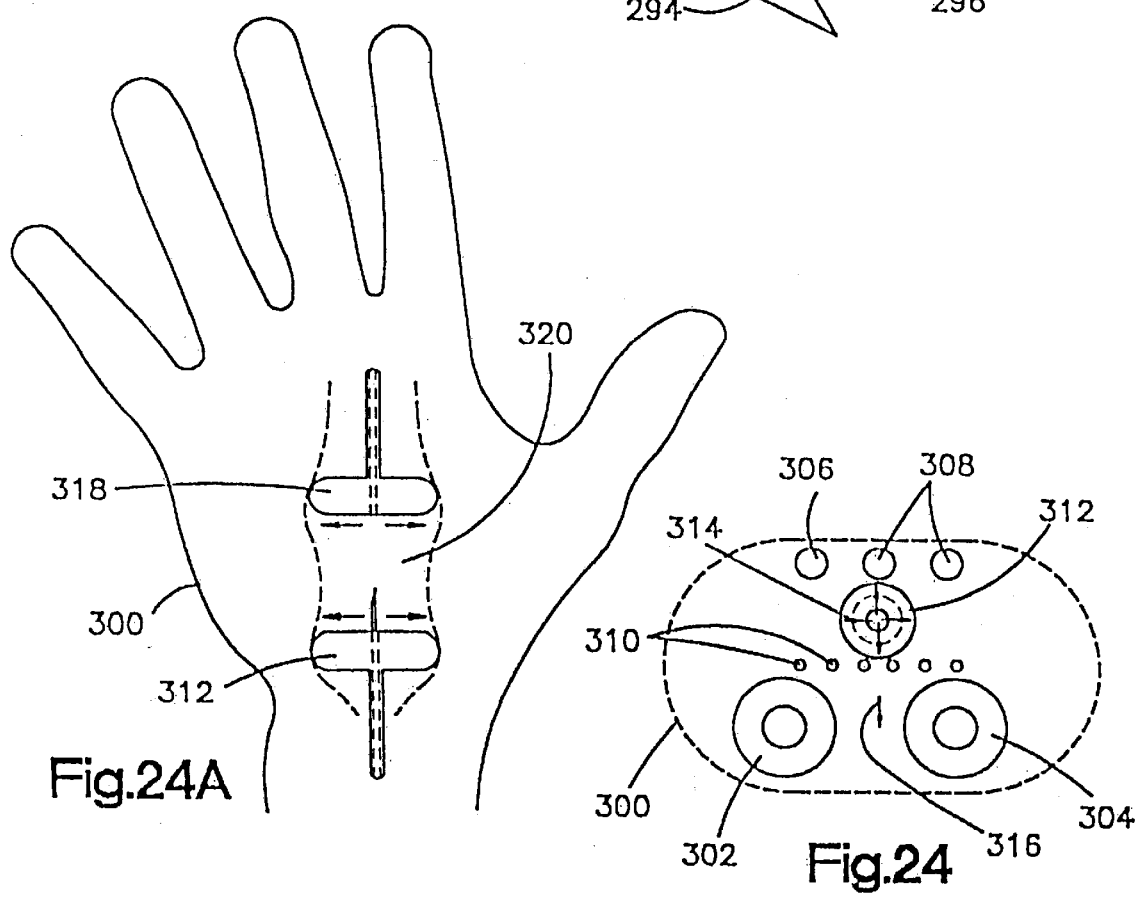

METHOD OF RETRACTING SOFT TISSUE FROM A BONE

This is a continuation of U.S. application Ser. No. 08/593,299, filed on Jan. 29, 1996, now U.S. Pat. No. 6,017,305 which is a continuation of U.S. application Ser. No. 08/419,851, filed on Apr. 10, 1995, abandoned, which is a continuation of U.S. application Ser. No. 08/216,097, filed on Mar. 22, 1994, abandoned, which is a continuation of U.S. application Ser. No. 08/054,416, filed on Apr. 28, 1993, abandoned, which is a divisional of U.S. application Ser. No. 07/487,645, filed on Mar. 2, 1990, now U.S. Pat. No. 5,331,975. The priority of these prior applications is expressly claimed and their disclosure is hereby incorporated by reference in their entirety.

BACKGROUND OF THE INVENTION

1. Technical Field

The present invention relates to tissue retractors for use in medicine. More particularly, the present invention relates to fluid operated apparatus for use in moving apart abutting tissues, during surgery, in order to create a space between the tissues to improve visualization and for increased working space during open surgery and fiberoptic assisted surgery.

2. Description of the Prior Art

Current methods used for retracting tissue and improving visualization are mechanical separation using metal retractors during open surgery or the direct pressure of an unconfined flow of fluid such as water or $CO_2$ during fiberoptic surgery. a typical mechanical external fixator has pins driven through the bones and mechanically distracts the elements of the joint. Problems with the water method include fluid extravasation including into and through the tissue itself. Increased pressure and swelling result in the area, resulting in edematous or swollen tissue. Excess pressure from mechanical refractors may cause necrosis or tissue death. With these methods, it is impossible to monitor the pressure being applied to the body tissues, and tissue damage or necrosis can result.

While operating from within the body, i.e., fiber optic assisted surgery as opposed to open surgery, there is no known way to selectively move or retract tissue, either hard tissue such as bone or soft tissue, out of the way to improve visualization. No device in use adequately allows a surgeon to create an actual space or expand a potential space in the body, by separating adjacent layers of tissue. The prior art does not disclose a retractor that is powerful enough and made of a material that is strong and resilient enough to, for example, separate tissue planes from within. Such a device, especially in the field of fiber optic surgery, would allow a surgeon to visualize and operate without using the conventional bulky and awkward mechanical refractors that require large open incisions. Such a device would also permit working within the body without damaging a great deal of tissue in the path between the skin opening and the working area, by minimizing the external orifice or skin incision.

SUMMARY OF THE INVENTION

The present invention is a system of refractors that a surgeon can use to take potential spaces within the body and turn them into existing spaces safely and easily and controllably in order to safely visualize appropriate tissue and operate. The retractor selectively moves appropriate tissue out of the way to enable a surgeon to see and work better within the body, and selectively moves body parts such as joint parts or soft tissue planes in order to create a space between the tissues for visualization and for working.

The retractor of the present invention include a fluid-operated portion such as a balloon or bladder to retract tissue, not merely to work in or dilate an existing opening, as for example an angioscope does. The fluid-filled portion is flexible and, thus, there are no sharp edges that might injure tissue being moved by the retractor. The soft material of the fluid-filled portion, to an extent desired, conforms to the tissue confines, and the exact pressure can be monitored so as not to damage tissue. The expanding portion is less bulky and more compact, and the pressure it applies at the tissue edges can stop bleeding of cut tissue. These are all features not possessed by a conventional mechanical retractor.

With a typical mechanical retractor, the opening in the skin and thence inwardly must be larger than the surgical area being worked upon, in order to be able to get the mechanical retractor into position. The surgeon must damage a large amount of tissue that may be healthy, in order to expose the tissue to be worked on. The retractor of the present invention minimizes damage to tissue in the way of the tissue the surgeon needs to expose, which was previously cut in a large open exposure. With the retractor of the present invention, the opening at the skin is smaller at the skin where the device is inserted and wider at the location inside the body where the retractor is expanded. The retractor is first placed into the body in an unexpanded condition, and then, as it is expanded, pushes tissue out of the way in deeper layers of the body one can see and safely operate on affected tissue. Thus, less undesired tissue damage occurs.

The bladder is pressurized with air or with water or another fluid. The fluid used in the bladder must be safe if it accidentally escapes into the body. Thus, besides air, such other fluids as dextrose water, normal saline, $CO_2$, and $N_2$ are safe. The pressure in the bladder is monitored and regulated to keep the force exerted by the retractor at a safe level for tissue to prevent tissue necrosis. The retractor can exert a pressure on the tissues of as high as the mean diastolic pressure of 100 mm of mercury, or higher for shorter periods of time, while still being safely controlled. Typical inflatable devices such as angioscopes do not have anywhere near the strength, or the ability to hold enough fluid pressure, or shapes to retract tissue as described herein. As compared to prior art devices, the retractor of the present invention operates with grater pressure within the bladder, since it is made of stronger materials such as Kevlar or Mylar which may be reinforced with stainless steel, nylon, or other fiber to prevent puncturing and to provide structural shape and support as desired. Such materials are strong enough to hold the necessary fluid pressure of about several pounds or up to about 500 mg Hgor more and exert the needed force on the tissue to be moved. The choice of material is well within the ability of one familiar with such materials and accordingly will not be gone into in further detail herein. The present retractor is thus able to exert substantially more force on adjoining tissues than a prior art device. The shapes of the refractors are specific for each application, and may include separate variable chambers which are sequentially controllable, to control the direction of tissue retraction.

GENERAL DESCRIPTION OF THE INVENTION

The fluid-filled portion of the retractor is preferably a unitary portion such as a bladder. In this case, the bladder is expanded with the introduction of fluid under pressure. Alternatively, the fluid-filled portion of the retractor may include a series of prongs or filaments that expand radially outwardly upon the introduction of fluid under pressure. The prongs themselves may be expandable, or there may be an expandable portion located centrally of all the prongs which, when it expands, forces the prongs outwardly.

Typically, the height of the bladder, that is, its width or transverse dimension, is significantly greater than its length (axial or longitudinal dimensions. The bladder expands primarily in width only, not in length, although the shape will vary with the application. This is in accordance with the purpose of the device which is to enable the separation of adjacent tissue layers to, for example, allow improved visualization in front of a scope inserted between the tissue layers.

The retractor of the present invention can be used to direct or position the end of a scope relative to the tissue walls. The retractor can also be used to stabilize the end of a scope. When a camera is being used via the scope, the scope often moves or jumps around because of the flexibility of the end of the scope. This is prevented by inflating bladders at the tip or along the shaft of the fiberoptic scope to control the direction of the tip of the scope and thus stabilize the scope leaving both hands free to work and providing a stable image for the surgeon.

Surgeons operate along tissue planes. Once a surgeon finds a tissue plane, he dissects along it, starting the separation process with the knife. The retractor holds the tissue layers apart and helps and eases in defining and further separating the tissue layers as the surgeon operates along the tissue planes, helping to spread and define the planes. The retractor helps to separate the tissue layers, increasing the space for operating, and improving the surgeon's ability to separate and visualize, leading to better and safer surgical technique.

A preferred use for the present retractor is in the field of fiber optic surgery, including endoscopy, arthroscopy, laparoscopy, etc., which require looking into and operating within a limited space with a fiber optic light and camera. The open or existing spaces in joints are generally too small to permit easy operation and visualization. In the prior art, only direct (unconfined) water or air pressure is used to expand the joint capsule or tissue in the joint. This may actually push tissue in front of the scope, obscuring vision. The present retractor distracts a joint directly to make it easier to see inside (around) the joint. A sleeve which can be a malleable or rigid sheath may optionally be provided to protect the tissue as the bladder is slid in and out of the end of the cannula once in the work area within the joint. The bladder expands into an area of soft tissue, for example, the bursa, and pushes it out of the way. The bladder can be left in place during the operation, or it can be deflated and removed, and the arthroscope and other instruments can be put into the space created.

An alternative preferred use for the retractor of the present invention is to operate in a joint of the spine, and specifically between two vertebrae. The retractor is used to spread two vertebrae apart to enable removal of the spinal disc from between the vertebrae.

Other uses of the retractor are as an occluding device to stop blood flow from an anastomosis or angioscopic procedure, or to stop backflow (retrograde flow) of stomach or colon contents. The retractor of the present invention is also suitable for use in the tempomandibular joint. Specifically, a dentist or oral surgeon uses an appropriately shaped retractor to hold open the jaw of a patient while the dentist or oral surgeon works: on the mouth of the patient. The inflatable retractor is much more comfortable to the patient than a rigid metal or plastic device, it conforms to the jaw structure rather than pressing unevenly against it, and lessens fatigue. Thus, it is safer for the dentist by safely maintaining the two rows of teeth spaced apart and by increasing visibility for working, while at the same time being easier for the patient.

The retractor can also be a useful diagnostic tool. The strength or pressure or resistance of tissue can be measured by the pressure required to move it.

The bladder may be a bellows type device in which the material does not stretch but which expands when pressurized from within and which is collapsed by the use of suction. In this case, it would preferably be made of a polymer of the class including Kevlar or Mylar fabric for strength and structural integrity. The bladder may generally also be made from any very thin walled polymer.

The bladder may also be made from a biocompatible and/or biodegradable material, so that if it can not be removed from the body for some reason, or if the surgeon desires to keep the bladder in place in the body for a period of time, it will not damage the tissue and may eventually be resorbed into the body. Such a biodegradable bladder may be left under the skin postoperatively to stop postoperative bleeding or to keep tissue expanded. Alternatively, the bladder may made of a stretchable material which stretches when pressurized from within, and then collapses partially of its own accord when depressurized or also with the help of suction. The retractor may be transparent for better visibility, but it need not be for some applications. Also, the retractor can be disposable. The material choice is within the skill of the art. One surface of the bladder may be made of or have thereon a reflective surface to reflect light to see around a corner.

The retractor can be used as a joint jack, that is, to distract a joint from within in one area and provide ease of access through the joint. Less damage to the joint occurs if the tissue edges are spaced apart during a procedure. When placed between two joint surfaces it pushes them apart from within, increasing the space available for visualization and/ or the working space. The retractor stabilizes a joint when expanded because it forces the tissues to remain in one place.

Another use is to look directly at a neurovascular bundle, retract it out of the way, and then operate around it. For example, the surgeon can go into the back of a knee, inflate the retractor, identify the neurovascular bundle and then be able to work around it. The task is made easier by the ability to separate tissue layers from within. One may cup the tissue then push it out of the way, in the nature of an umbrella opening, to protect vital tissues to operate safely around them.

Depending on the application, the retractor can be left in place while the work (or looking) is being done, or it can be deflated and then taken out to allow a scope or other instrument to be put in. Some tissues will stay in place to allow this latter function, after the space has been created with the retractor.

A most typical construction for the retractor of the present invention is an inflatable bladder situated on the end of a shaft which may be flexible or rigid which is pushed through an extra opening in a scope or cannula, or through a separate portal, and which expands at the end of the shaft.

The retractor can be located on a scope, either on the end thereof or movable axially through a channel along the length of the scope. The retractor can alternatively be mounted on a cannula. The retractor can be mounted on a separate shaft passing through an existing channel in a cannula; it can be inserted through a separate hole in the cannula or the scope; or it can be inserted through a separate opening in the body. The shaft with a retractor on the end can be pushed or slid through the cannula, side by side with a scope. Alternatively, the bladder can expand out of, then recess back into, a groove on a cannula or scope. The retractor can be used to create a space right by the scope, or possibly at a location spaced from the end of the scope. The bladder itself can be round, eccentric, oval, conical, wedge-shaped, U-shaped, curved, angled, or it may be in any shape desirable to optimize the particular application. The bladder may be irregularly shaped when inflated, that is, it may expand to a greater radius in the area where it is desired to look (where greater exposure space is needed).

Vacuum can be used to deflate the bladder. The bladder may then be removed by sliding it out the portal directly.

In one embodiment the retractor includes a spring loaded sleeve that slides axially over a plurality of plates or prongs, plastic or metal. A centrally located motive force is provided to move the prongs outwardly to retract the tissue, which force may be mechanical or a separate inflatable device. Alternatively, each filament is a tube that expands and straightens out as air pressure is added (as it is inflated) and, thus, moves radially outwardly to retract adjoining tissue. The filaments plates or prongs are controllable and covered by a sheath which slides off them proximally axially to allow them to be inflated and expand, and, then after they have been deflated, slides distally along the shaft over the filaments to cover them and allow the device to be moved through the body. When the sleeve retracts the prongs or filaments expand radially outwardly to push tissue away from the scope to improve visualization.

The retractor can be disposed at the end of a flexible sheath. The retractor can be directable with cables, or with compressed air, to turn or bend in a certain direction.

The present invention also provides a new type of self-retaining retractor that is more compact and is disposable for use in open surgery. The retractor is used to hold tissues laterally, pushing tissue edges apart. For such an application, the retractor includes a U-shaped bladder that is a tube that acts like a spring and, under high pressure, attempts to straighten itself out when inflated. The deflated tube-like structure is first properly positioned within the wound. As the retractor is inflated, it tries to straighten out, and thus opens the wound. As it presses on the edges of the wound, it compresses tissue edges, giving a hemostatic effect. For example, if the retractor is put vertically into a wound, it expands the deep tissues. The retractor can also use the inflatable bladder to push apart metal or plastic plates to push apart tissue.

BRIEF DESCRIPTION OF THE DRAWINGS

Further features of the present invention will become apparent to those skilled in the art to which the present invention relates from reading the following specification with reference to the accompanying drawings, in which:

FIG. 6 is a schematic view of a retractor shown mounted on the end of a cannula and having an opening therein for a scope to pass through.

FIG. 7 is a diagram of a fluid supply system for operating a retractor.

FIGS. 8 and 8A are views illustrating the use of a retractor to position the end of a scope.

FIG. 15 is a schematic view showing two refractors being used together to create an open working space in a blood vessel or a working space from potential space created between the two expanded bladders.

FIG. 16 is a schematic view illustrating the relatively large size of an expanded retractor compared to the relatively small size of the percutaneous incision.

FIGS. 17 and 17A–C are schematic views showing a retractor used for percutaneous bone access.

FIGS. 22 and 22A are schematic views illustrating the use of refractors of a certain shape to create a visualization and working space.

FIG. 23 is a schematic view illustrating a retractor having a reflective surface thereon; and FIGS. 24 and 24A is a series of views illustrating a retractor of the present invention suitable for use in carpal tunnel surgery.

DESCRIPTION OF PREFERRED EMBODIMENTS

Figure 1:
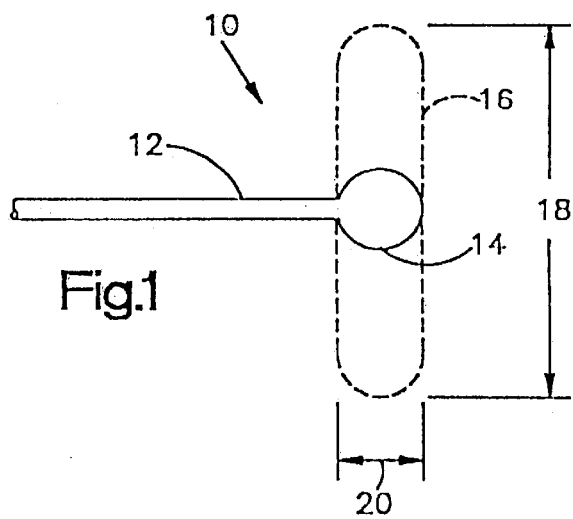
FIG. 1 is a schematic view of a retractor in accordance with the present invention shown in the unexpanded and expanded conditions.

FIG. 1 illustrates schematically a retractor 10 in accordance with the present invention. The retractor 10 includes a fluid supply structure 12 and an expandable balloon or bladder 14 located at or near the end of the structure 12. The bladder is expandable, under the force of fluid under pressure, from an unexpanded condition as indicated in full lines at 14 to an expanded condition as shown in broken lines at 16. In the expanded condition, the transverse dimension 18 of the bladder 14 is significantly greater than its transverse dimension before expansion. The longitudinal dimension 20. Also, in the expanded condition, the transverse dimension 18 of the bladder 14 is significantly greater than its longitudinal dimension 20.

Figure 2:
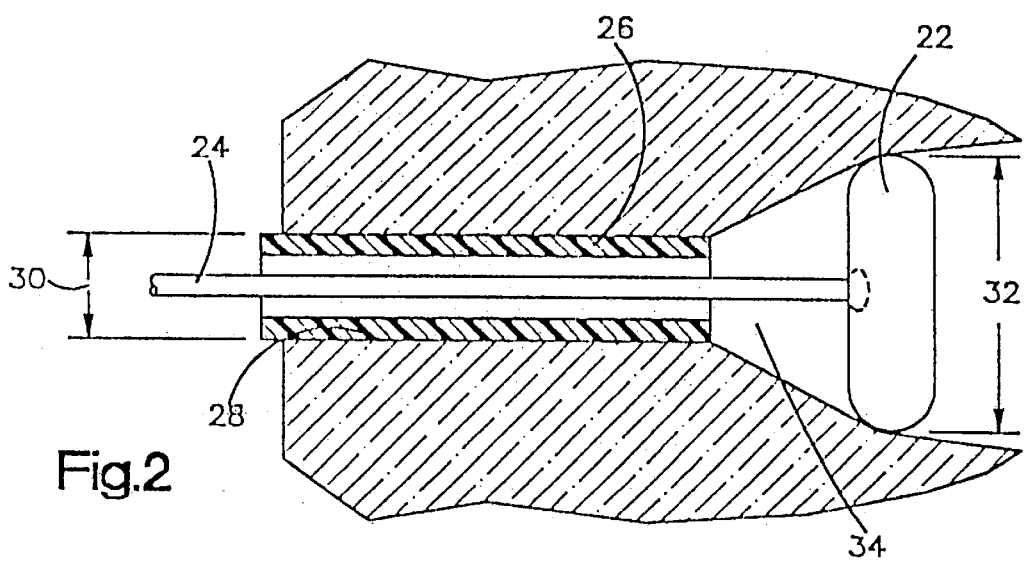
FIG. 2 is a schematic view of a retractor extending through a cannula and mounted on the end of a separate shaft.

When the bladder of the retractor is expanded inside the body, it retracts tissue. As soon in FIG. 2, a bladder 22 is mounted on the end of a separate shaft 24 within a cannula or scope 26. The cannula or scope 26 has been inserted into the body through an opening 28 in the skin (either preexisting or made in situ) which has a transverse dimension 30. The bladder 22 when in its unexpanded condition as shown in broken line is smaller than the dimension 30 of the body opening, but when expanded, it expands to a dimension 32 which is significantly greater than the dimension 30. An actual space or working space 34 is formed which was not present before the expansion of the bladder.

Figure 3:
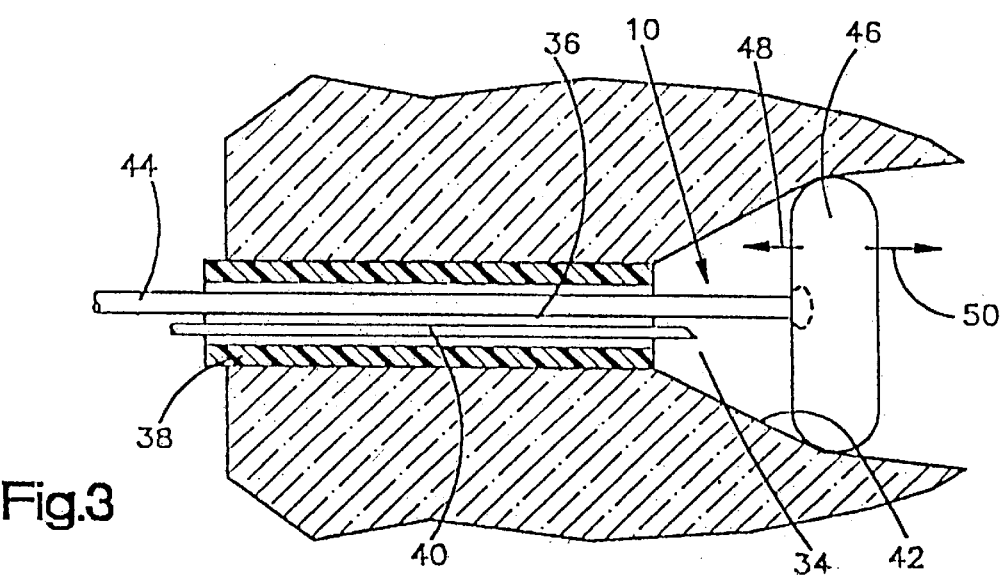
FIG. 3 is a schematic view similar to FIG. 2 illustrating the use of a fiber optic scope with the retractor.

The newly formed working space may be used, for example, for better use of a fiber optic scope as, illustrated in FIG. 3. In FIG. 3, a retractor 10 is passed through an opening 36 in a cannula 38. A fiber optic scope shown schematically at 40 is also passed through the cannula 38. The cannula 38 is inserted into the body through an opening in the body tissues 42 that is only as large as the outer diameter of the cannula 38. The retractor 10 is then inflated, with air or another fluid being supplied through a rigid or flexible shaft 44 to an expandable bladder 46. The bladder 46 expands transversely, retracting the tissues 42 transversely and creating a working space 34. By axial manipulation of the shaft 44, the bladder 46 is movable either toward the end of the scope 40 in the direction as indicated by the arrow 48, or away from the end of the scope 40 as indicated by the arrow 50, as desired. Such manipulation of the retractor can selectively move and place the adjoining body tissues where the surgeon wants them to enable better use of the scope 40 by the surgeon.

Figure 4:
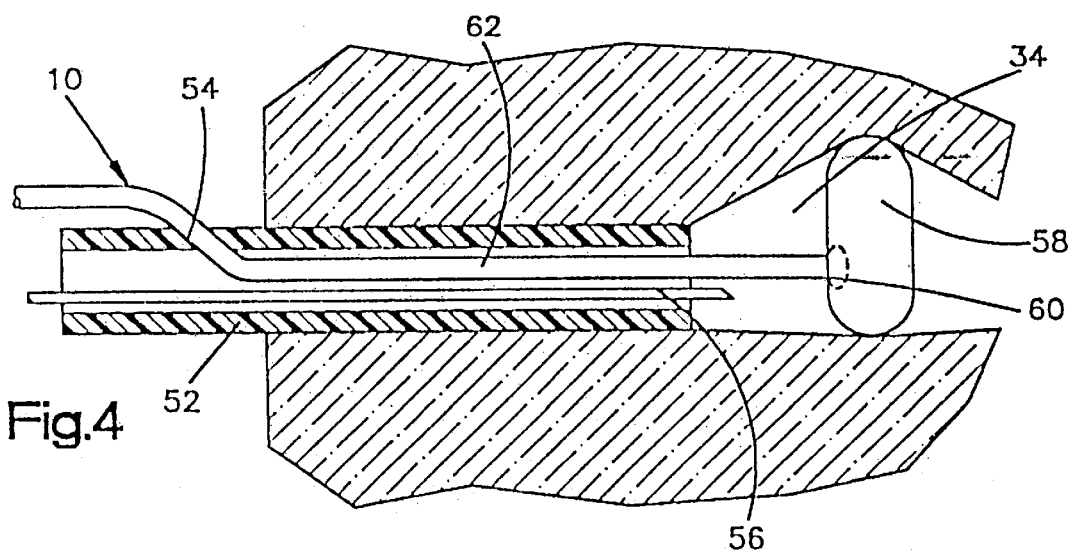
FIG. 4 is a schematic view showing a retractor inserted through a separate side opening in a cannula.
Figures 5A, 5B, 5C, 5D, 5E:
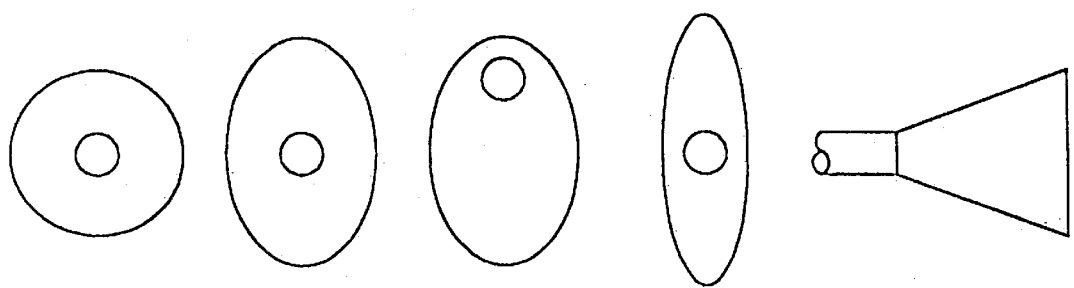
FIGS. 5A–E are schematic views of a few of the many and various shapes in which the inflatable portion of the retractor may be formed.

As shown in FIG. 4, the retractor 10 may be inserted into a cannula 52 through a separate opening 54 therein. The opening 54 is shown on the side of the cannula 52, although, of course, it may be on the end of the cannula as is typical. Alternatively, the retractor 10 may be inserted into the body through an opening in the body tissues separate from the opening through which the fiber optic scope is inserted. Either of these options allows for greater flexibility in the insertion and positioning of the retractor 10 relative to the other instruments being used such as the arthroscope.

Also as indicated in FIG. 4, the bladder 58 may be eccentric or eccentrically located relative to the opening 60 at the junction between the bladder 58 and the shaft 62. This is accomplished by using known techniques to form the bladder 58 of a material, construct ion, and shape such that it expands into the eccentric shape as illustrated in FIG. 4 when inflated by fluid under pressure through the shaft 62. In this manner, an improved visualization and working space 34 is created which is eccentrically located relative to the other instruments being used. This may be preferable when the surgeon is using an angled scope.

FIG. 4 is illustrative of the fact that the bladder of the retractor of the present invention may be formed so as to expand into any particular shape as desired for the particular application. This feature is also shown schematically in FIGS. 5A through 5E that illustrate, respectively, retractor bladders that assume in their expanded states in round, oval, eccentric, oblong, and conical shapes. Such shapes may generally be called "nonuniform" shapes for purposes of the present invention, and refractors with such a shape will expand in a "nonuniform" manner. Such shapes may include, for example, wedge or U-shaped filaments which collapse at the skin, then expand at deep tissue planes for visualization and working space. The bladder may also cup and protect vital tissues such as nerves and arteries while working on other tissues such as muscle.

Figure 6:
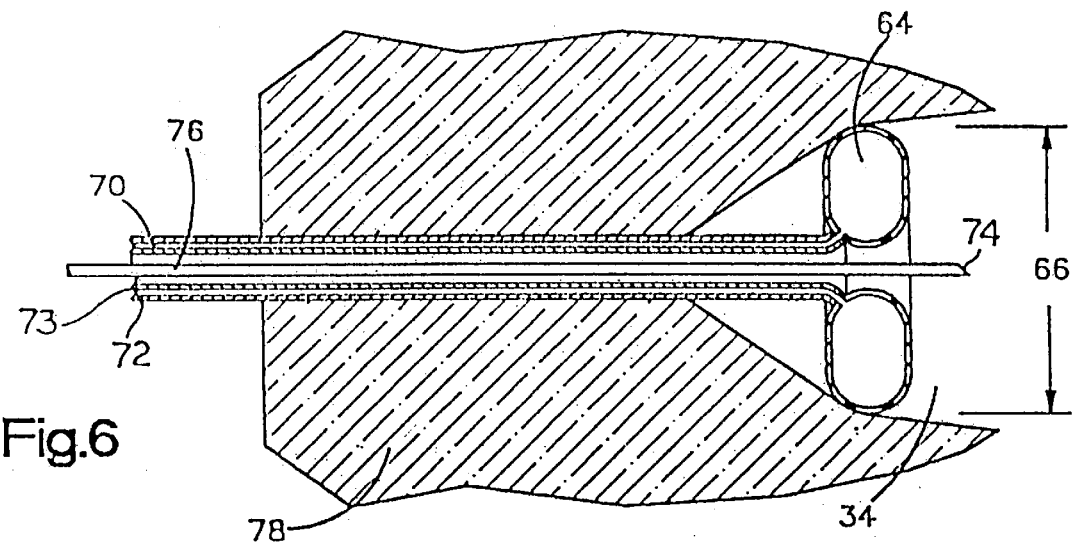

Another typical form of construction is illustrated in FIG. 6, which shows a bladder 64 that in its expanded condition assumes a toroidal shape. Again, the width 66 of the bladder 64 is significantly greater than its length 68. The bladder 68 is expanded by fluid under pressure received through a fluid channel 70 formed between a cannula or scope outer wall 72 and inner wall 73. By virtue of the toroidal shape of the bladder 68, the leading end 74 of the scope 76 may be passed axially completely through the retractor into the working space 34 which has been created in the tissues 78. Such a bladder 64 may also be mounted on a separate shaft inserted through the scope of the cannula.

In all cases, the fluid pressure within the bladder of the retractor is monitored and controlled to keep the force exerted by the retractor at a safe level for tissue to prevent tissue necrosis. As indicated schematically in FIG. 7, a retractor 10 is supplied with fluid under pressure from a fluid pressure source 80 via a fluid supply line 82. A regulator 84 controls the supply of fluid to the retractor 10. A pressure sensor 86 is located within the retractor 10 and senses the pressure of the fluid within the retractor 10. The pressure sensor 86 sends a signal which is representative of the fluid 10 pressure within the retractor 10, via wiring 88, to a monitor 90. The monitor 90 is connected via control wiring 92 to the pressure regulator 84. The pressure of the fluid within the retractor 10 may thus be monitored and controlled either manually or automatically by means that are well known in the art and so need not be described further herein. The source 80 of fluid supply may be, for example, the air pressure supply which is commonly found in hospital operating rooms.

By virtue of this ability to monitor the pressure within the retractor 10, the retractor 10 can also be a useful diagnostic tool. The strength or pressure or resistance of tissue to movement can be measured by the pressure required to move it.

FIGS. 8 and 8A illustrate the use of a retractor of the present invention to stabilize a fiber optic scope. The retractor 10 (FIG. 8) includes a bladder 94 that retracts the body tissues 96 away from the scope 98. Since the bladder 94 engages and pushes radially outwardly on body tissues 96 all around the scope 98, the retractor becomes fixed in position when it is so expanded. If the bladder 94 is fixed to the end of the scope 98, the retractor 10 thereby fixes the end of the scope 98 in position relative to the body tissues 96. When a camera is being used with the scope 98, the picture normally moves or jumps around because of the movability of the end of the scope 98. This is prevented by so using the retractor 10 to stabilize the scope 98, leaving the surgeon with both hands free to work and a steady view of the work area.

FIGS. 8 and 8A also illustrate how the retractor of the present invention can be used to control the placement of the tip of a fiber optic scope. The retractor 10 is formed with an eccentric bladder 94 that retracts the body tissues 96 away from the scope 98 to a greater distance in one direction than in another. Thus, by rotating the retractor 10, the surgeon can place the tip of the scope 96 closer to the body tissue 100 (FIG. 8) on one side of the working space 34, or to the body tissue 102 (FIG. 8A) on the other side of the working space 34. Such variable placement can, of course, also be attained via use of a retractor 10 that includes a bladder that can be expanded to varying shapes.

Figure 9:
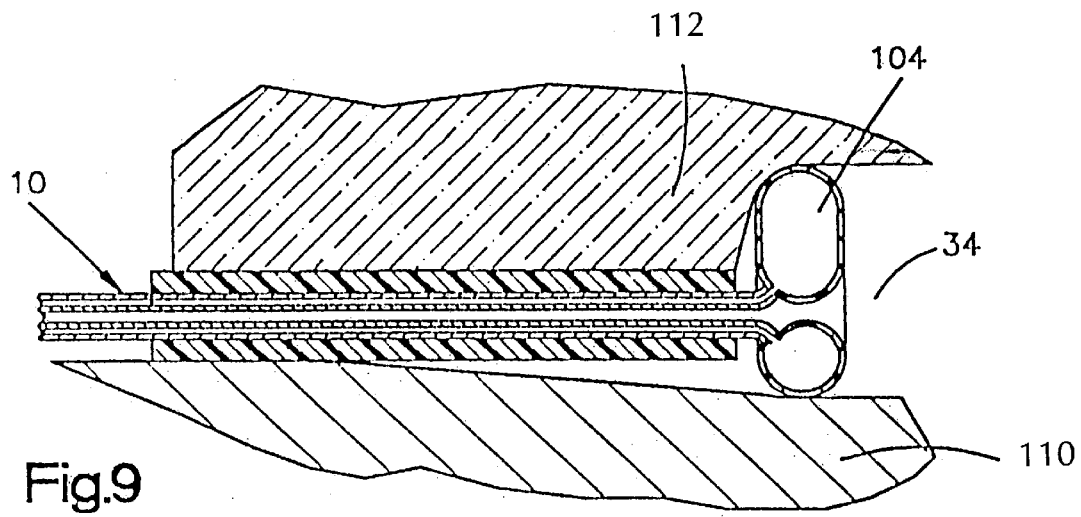
FIG. 9 is a schematic view illustrating the retraction of soft tissue from bone.

The retractor of the present invention has many uses in the surgical field. FIG. 9 illustrates the use of a retractor 10 to retract soft tissue from bone, for example, within a joint. The retractor 10 is inserted between the bone 110 and the soft tissue 112. The bladder 104 is then expanded. The soft tissue 112 is forced away from the bone 110. The surgeon may then use a fiber optic scope or other instrument to work within the working space 34 created by the retractor 10. The retractor of the present invention can provide the force needed to move the soft tissue 112 away from the bone 110 may vary between about 100 and 1000 mm Hg, and, thus, it is important to maintain the proper pressure between the two. The retractor 10 can do this since it operates on high fluid pressures of about 10 to 1000 mm Hg and it utilizes a high strength material such as Kevlar, Mylar, or another durable polymer such as Polylite®, a product of Reichhold Chemicals, Inc. This simple retraction of soft tissue from bone would otherwise be impossible.

Figure 10:
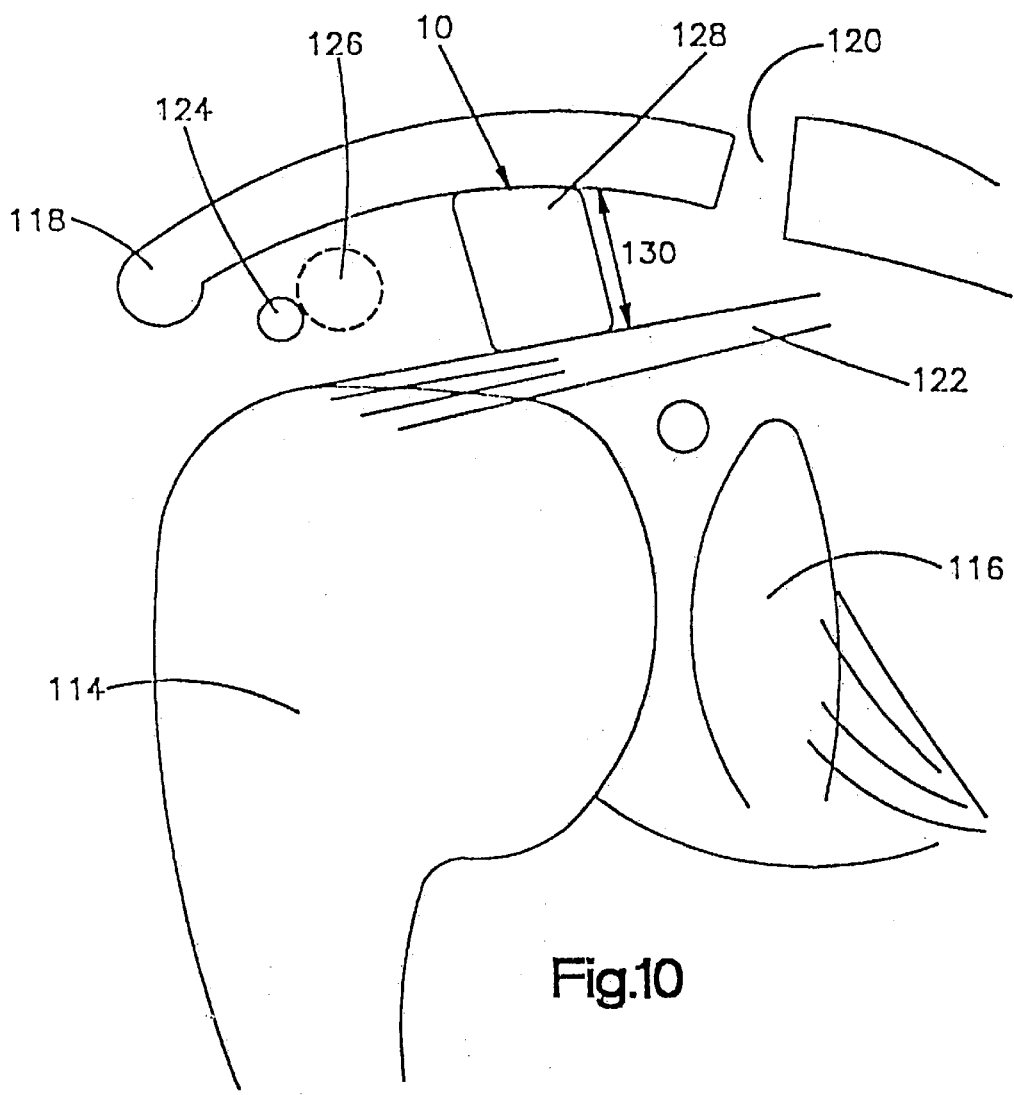
FIG. 10 is a schematic view of a retractor shown in use in a shoulder joint.
Figures 11, 11A:
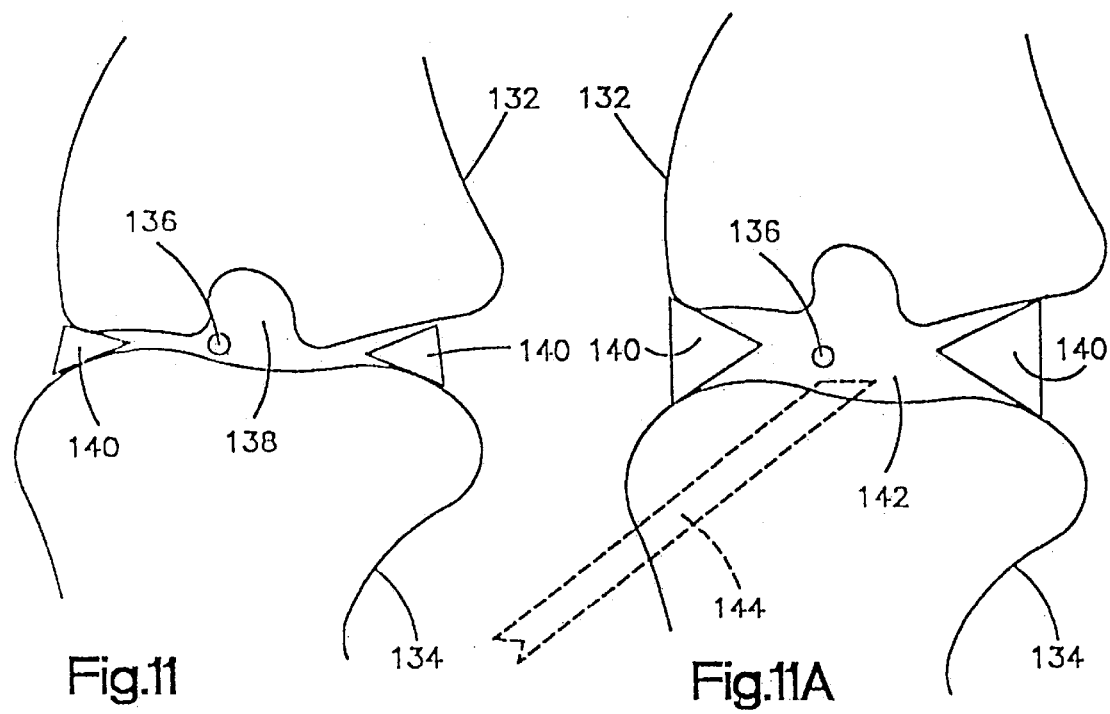
FIGS. 11 and 11A are schematic views of a retractor shown in use in a knee joint.

FIG. 10 illustrates the use of a retractor 10 to enable a surgeon to work within a shoulder joint. The joint includes the humeral head 114, the glenoid 116, the acromion 118, and the acromion joint 120. The rotator cuff 122 is attached to the humeral head 114. A scope 124 is inserted preferably from the back of the shoulder joint. In the prior art method, the acromion 118 can be separated from the bone from within the joint, in order to gain access to the rotator cuff, only by introducing an unconfined stream of water into the joint as indicated at 126. This method leads to the presence of water everywhere, including within the tissues themselves, and is not a desirable method. In accordance with the present invention, a retractor 10 with an expandable bladder 128 is simply inserted through a small incision in the skin and inflated to expand in the direction indicated by the arrow 130, thus retracting the tissue space. There is no unconfined fluid introduced into the tissue space, and the degree of separation of the joint is easily and safely controlled by controlling the pressure within the retractor 10.

FIGS. 11, 11A, 12, and 12A illustrate the use of a retractor 10 to enable a surgeon to better work within a knee joint. The joint includes femur 132 and tibia 134 and between them a neurovascular bundle 136 which the surgeon wishes to work on (or work around). However, the normal space 138 within the tissue space is so small as to make working within the joint very difficult or impossible. Accordingly, a retractor that is in the form of a wedge-shaped bladder 140 (FIGS. 11 and 11A) is inserted on one or both sides of the knee joint and expanded. The retractor expands in a straight or curved shape depending on its dimensions and easily separates the joint, creating a much enlarged working space 142 (FIG. 11A), enabling the surgeon to operate via any instrument such as the scope illustrated schematically at 144. In a similar manner, a surgeon can easily spread adjacent vertebrae in a spine to work on the spinal column, for example to remove a spinal disc or any other tissue or bone. The bladder 140 may also be formed with a curved-shape or otherwise custom fit for the particular application.

Figures 12, 12A:
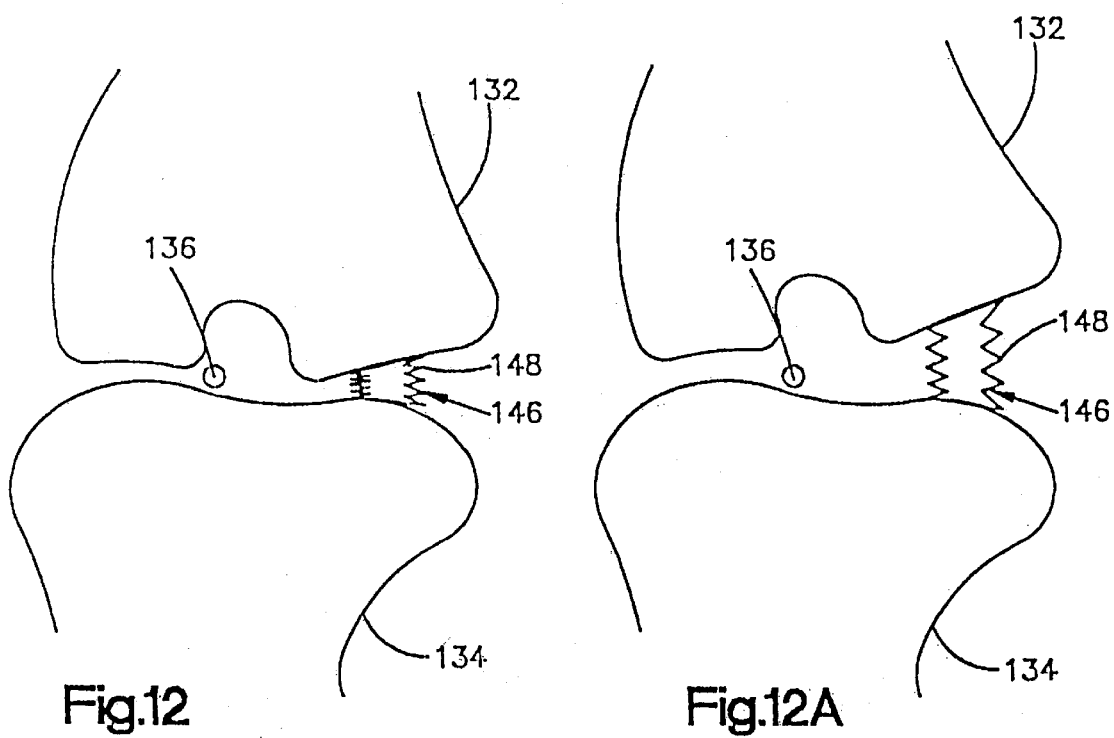
FIGS. 12 and 12A are schematic views of a second embodiment of a retractor shown in use in a knee joint.

The retractor 10 shown in FIGS. 12 and 12A operates similarly, with the exception that the bladder 146 is formed as a bellows type device which expands in an accordion-like manner. The material of which the bellows type bladder 146 is made does not necessarily stretch although it may somewhat, but rather the expansion comes primarily when the various surfaces are repositioned relative to each other. The accordion like ridges 148 may be made of differing degrees of resistance to straightening and flexing, in order to vary the rate and/or sequence of inflation of various portions of the bladder 146. Alternatively, the material of which the bladder 146 is made has areas of rigidity interleaved with areas of more elasticity, to provide the desired expansion effect. The ridges 148 may also be closure members that divide the bladder 146 into a plurality of separate inflatable chambers with valving therebetween, for sequential inflation. Such an accordion-like or bellows construction can provide greater stability in intermediate partially expanded) positions, and can have greater structural integrity.

Figure 13:
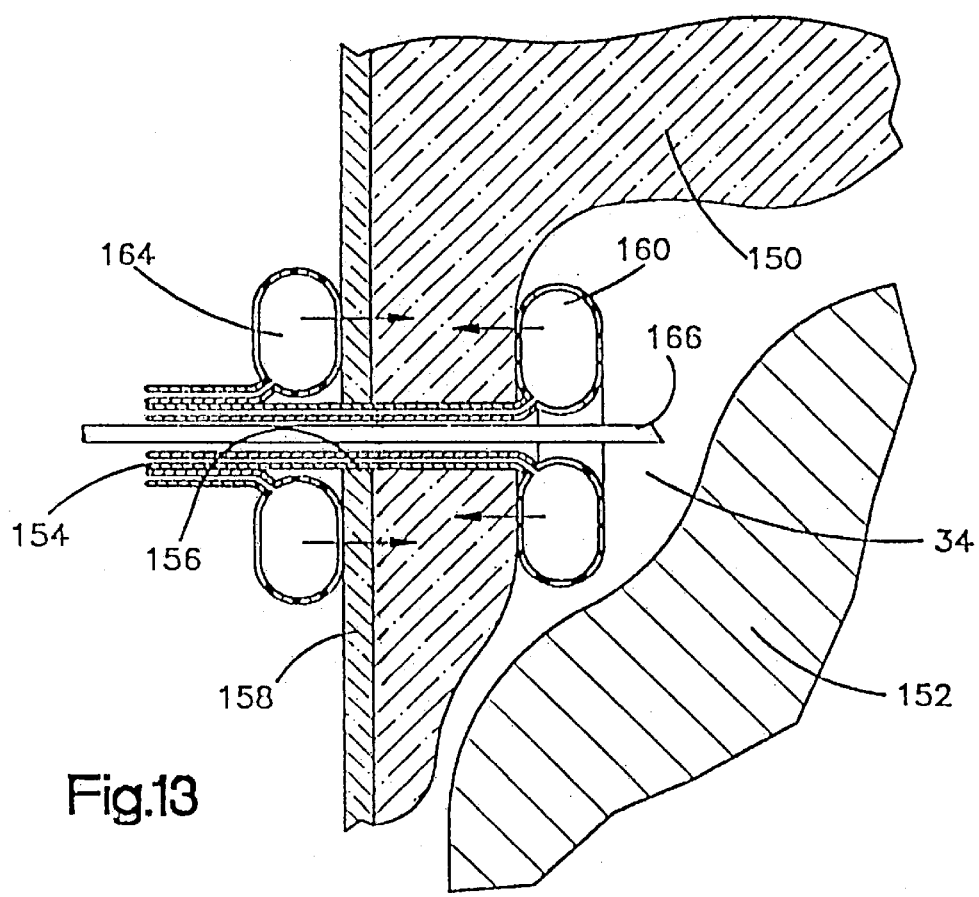
FIG. 13 is a schematic view illustrating the simultaneous use of two refractors to retract tissue.

FIG. 13 illustrates how a pair of refractors in accordance with the present invention can be used together to create a working space between them. In the operation illustrated schematically in FIG. 13, the surgeon desires to retract a fat pocket or tissue 150 away from a knee 152 in order to provide a working space 34 between them in which he can operate. A cannula 154 is inserted through a small opening 156 in the skin 158 and through the fat pocket or tissue 150. An inner bladder 160 is inflated inside the fat pocket or tissue 150, while an outer bladder 164 is inflated on the outside of the skin 158. Drawing the two bladders toward each other pulls the fat pocket or tissue 150 toward the skin and away from the knee 152, thus creating the enlarged working space 34. This enables the surgeon to operate comfortably with a scope or other instrument 166, while still performing the entire operation percutaneously as is, of course, desired, meanwhile stabilizing the instrument.

Figure 14:
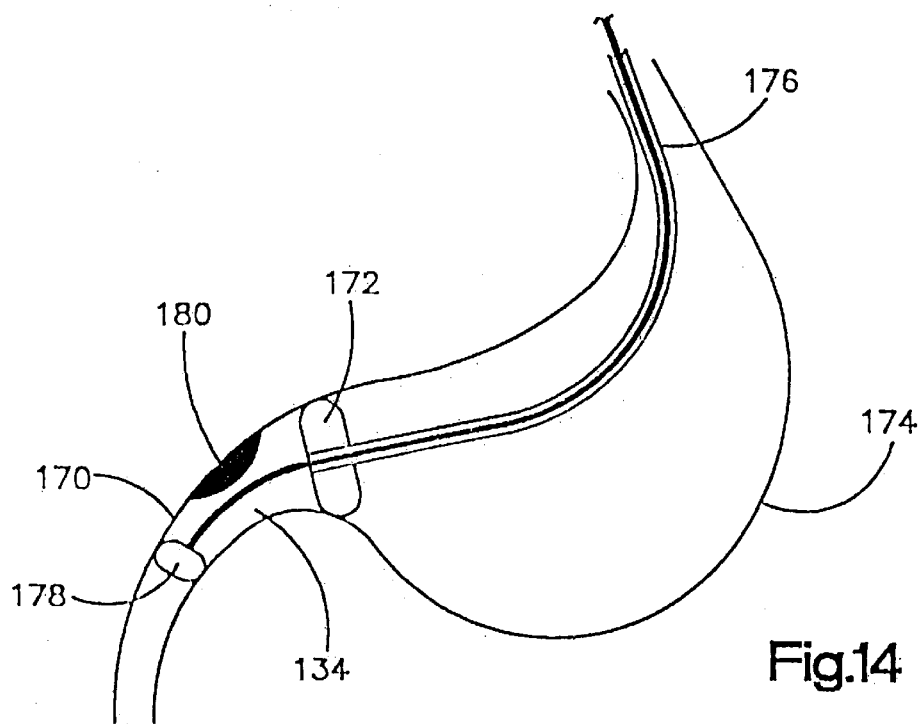
FIG. 14 is a schematic view illustrating the simultaneous use of two refractors to create an open working space in a digestive tract.

In a somewhat similar manner, two separate refractors can be used to create a working space in between the two refractors. For example, FIG. 14 illustrates the use of a pair, of refractors to create and maintain an open working space in a duodenum 170. A first retractor 172 is inserted through the stomach 174 on a scope or cannula 176 and is inflated at the upper end of the duodenum 170 to block it off from the stomach 174. A second retractor 178 is inserted through the stomach 174 on the scope or cannula 176 and is inflated lower on the duodenum 170 to block it off from the small intestine. An open working space 34 is thus created between the refractors 172 and 178. The working space may be maintained as long as both refractors 172 and 178 remain inflated. Such an open working space is advantageous to enable a surgeon to better work on, for example, a growth 180 in the duodenum 170. The retractor may also be used to block off an artery in a bleeding area of the bowel by direct pressure.

Similarly, FIG. 15 illustrates the use of a pair of retractor in accordance with the present invention to create a working space in a blood vessel. A first retractor 182 is inserted through a main blood vessel 184 on a cannula 196 and is inflated to block the vessel 184 from blood flow in one direction. A second retractor 188 is inserted through the vessel 184 on a separate shaft 190 through the cannula 186 and is inflated farther along the vessel 184 to block blood flow from a branch blood vessel 192. An open working space 34, free of blood., is thus created and is maintained as long as both refractors 182 and 188 remain inflated. Such an open working space can advantageously be used to enable a surgeon to better work, for example, with a scope 194 within the main vessel 184.

As noted above, an important advantage of the retractor of the present invention is that it can be used percutaneously to create a large actual space within the body while making only a small opening in the skin. This allows for percutaneous or fiber optic surgery in locations where heretofore only open surgery with its attendant disadvantages was possible. This feature is illustrated in FIG. 16 that shows in solid lines a retractor 10 for insertion through a cannula 196 into an opening 198 in skin 200. The retractor 10 is, at the time of insertion, no larger in diameter than the opening 198. However, once inserted into location subcutaneously, the retractor 10 can be expanded to the condition shown in broken lines to create a working space which as illustrated by the relative size of the arrow 202 is significantly larger than the opening 198 in the skin 200.

The retractor illustrated in FIGS. 17–17C uses a bladder that is longer than it is wide but which is hollow. To gain access to the surface 204 of a bone 206, a small opening 208 is formed extending through the skin 210 and the muscle 212. The opening 208 extends down to the surface 204 of the bone 206. A retractor 214 (FIG. 17A) is then inserted, in an unexpanded condition, into the opening 208 and down into contact with the surface of the bone. The retractor has an inner wall 215 and an outer wall 217 with a fluid space 219 between. The retractor 214 is then inflated, as seen in FIG. 17B, retracting the adjoining skin 210 and muscle 212 radially outwardly. The retractor 214 has a hollow cylindrical shape with an opening 216 in the middle (see FIG. 17C). The opening 216 is significantly larger than the opening 208. A surgical or other instrument can be inserted through the opening 216 from outside the body, into contact with the surface 204 of the bone 206, while the opening 216 is being maintained. Thus, a large opening can be temporarily created with only a small opening in the body tissue.

In a variation on the retractor shown in FIGS. 17–17C, a retractor like the retractor 214 is shorter and has a ring-shape when expanded. The retractor is slid into the body tissue over a small pin such as a K-wire that has been used to pinpoint the desired area. The retractor is slid in while deflated, then expanded when at the desired location inside the body. The inner diameter when expanded, though slightly less than the outer diameter, is still much larger than the size of the pin, forming a large working and visualization space for the surgeon. The surface of the retractor may be roughened, ribbed, or serrated for better gripping power to keep the retractor in place while expanded.

Figure 18:
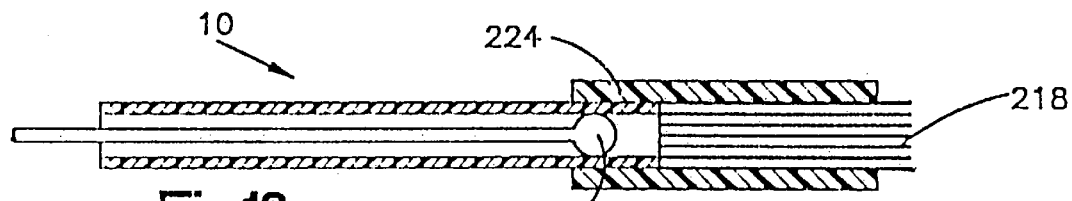
FIGS. 18 and 18A–C is a series of schematic views illustrating another embodiment of the fluidexpandable portion of the retractor of the present invention.
Figure 18A:
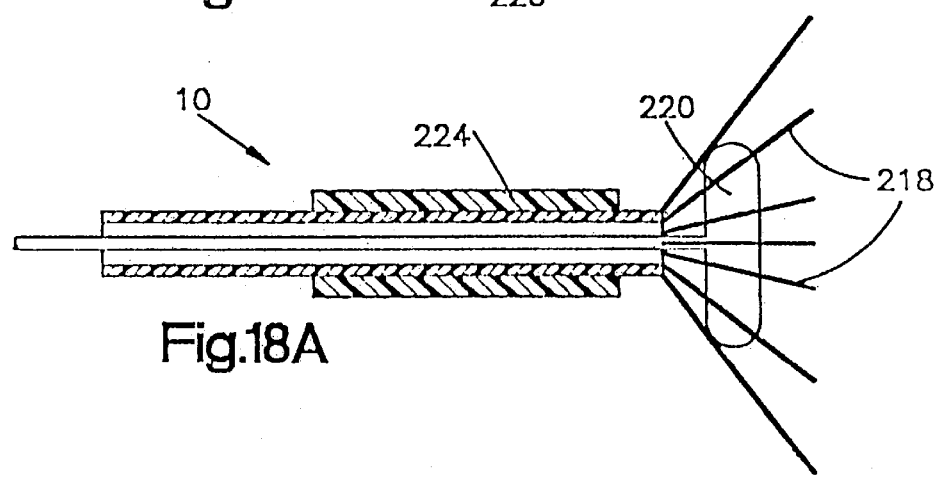
Figure 18B:
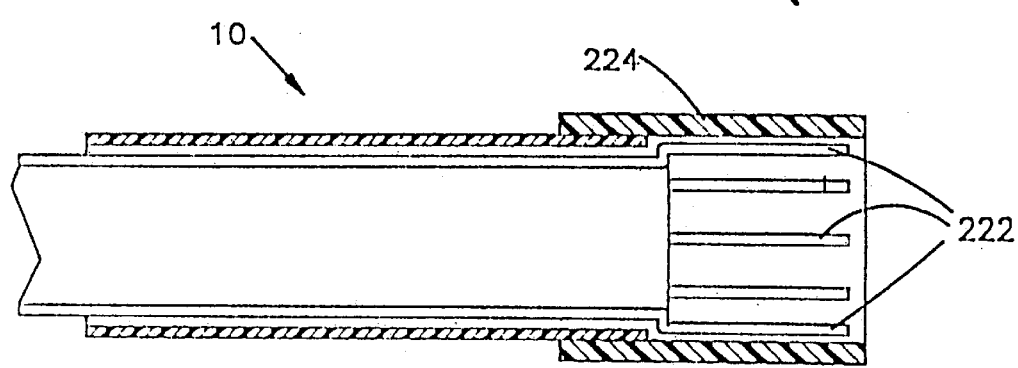
Figure 18C:
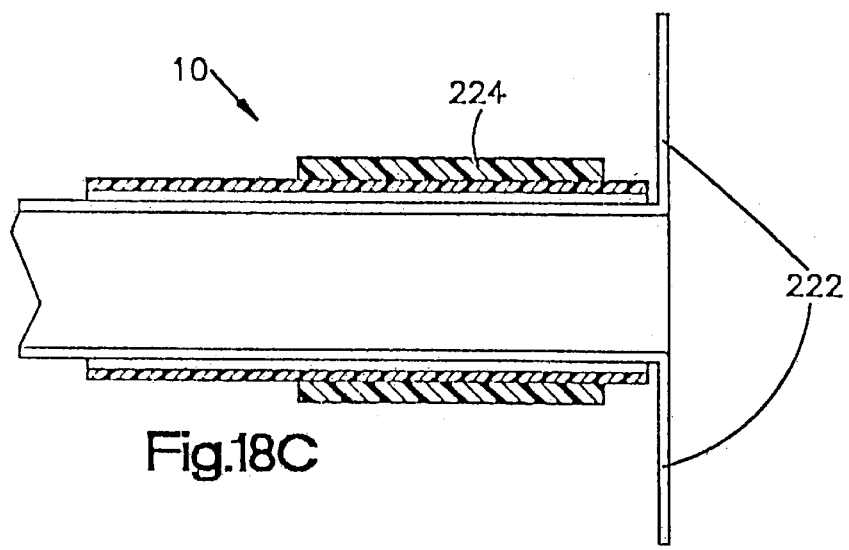

In another embodiment of the invention illustrated in FIGS. 18–18D, the one-piece bladder of the retractor 10 is replaced by a series of plates or filaments that are expanded radially or conically outwardly to retract the adjoining tissue. These plates or filaments may, as illustrated in FIGS. 18 and 18A, be rigid or semi-rigid elements 218 which are expanded radially outwardly by a centrally located positioner 220 which may be mechanical or which may be air-operated such as an expandable bag. This is in the nature of a spring loaded umbrella with a sleeve which slides over the ribs of the umbrella, which ribs open and expand outwardly when the sleeve is pulled back. Alternatively, as illustrated in FIGS. 18B and 18C, the filaments 222 are hollow inflatable elements which themselves inflate upon application of fluid under pressure to the retractor 10, straightening out as they fill with pressurized fluid. In either case, a sleeve 224 is preferably provided to protect and help locate or position the radially movable elements. The sleeve 224 slides axially. The plates or filaments are covered by sheath 224, which slides off them proximally axially to allow them to be expanded radially outwardly to push tissue away from the scope to improve visualization. After deflation, the sleeve 224 slides distally along the shaft over the filaments to cover them and allow the retractor 10 to be moved through the body. A sleeve such as the sheath 224 can also be employed in conjunction with a unitary bladder. In either event, the sleeve can be rigid or can be flexible.

Figure 19:
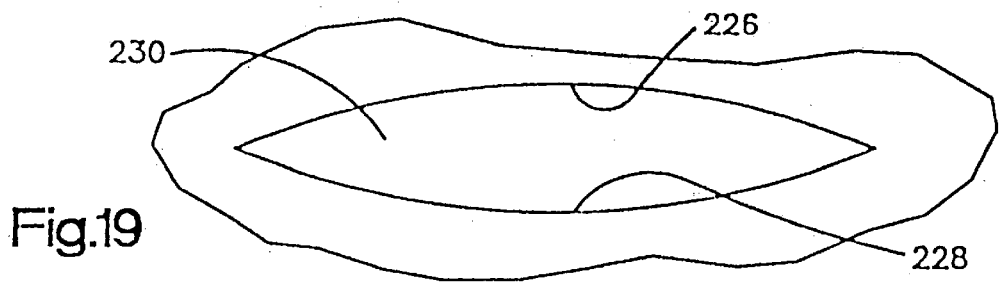
FIGS. 19 and 19A–C is a series of schematic views illustrating a retractor of the present invention suitable for use in open surgery.
Figure 19A:
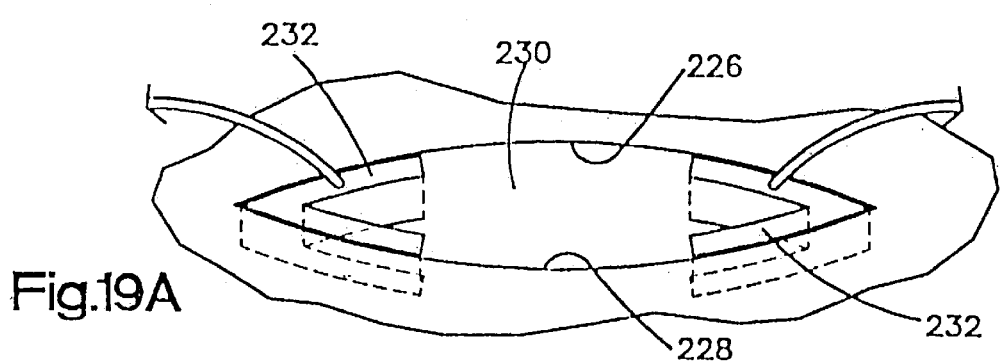
Figure 19B:
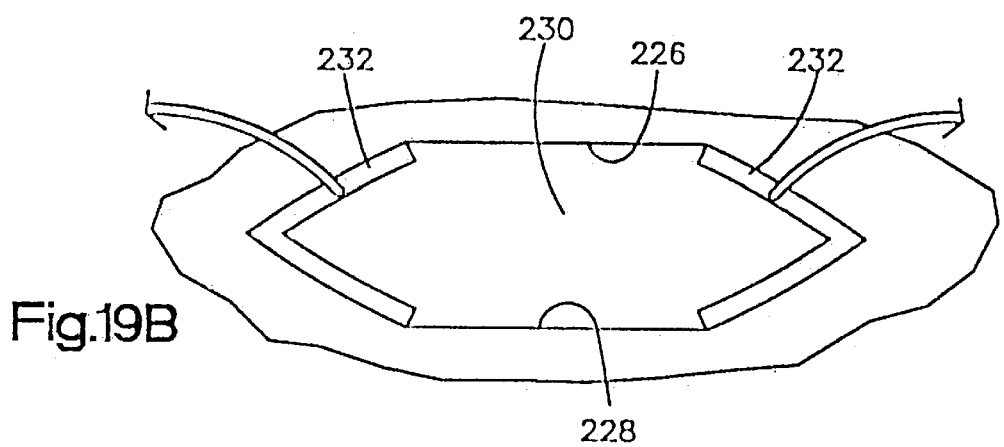
Figure 19C:
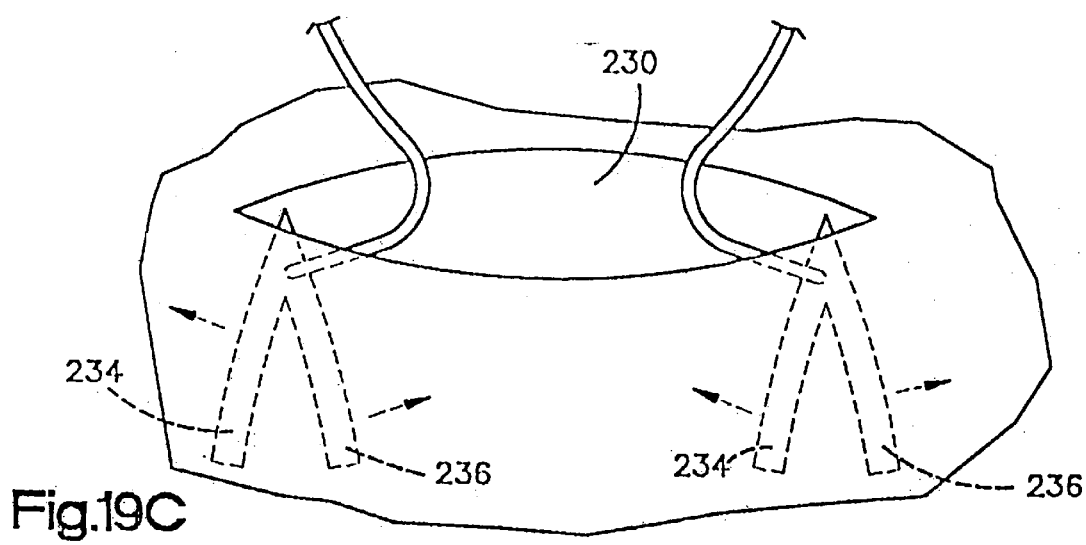

Retractors in accordance with the present invention can also be used for open surgery. FIGS. 19–19C are a series of schematic views illustrating the use of a retractor of the present invention in open surgery. The retractor is used to hold tissues laterally, pushing tissue edges apart. FIG. 19 shows the edges 226 and 228 on either side of an open surgical incision or opening 230. As seen in FIG. 19A, an open surgery retractor 232 has been inserted down into the incision 230. The retractor 232 is in the form of a hollow expandable tube that is bent into a V-shape or a U-shape for insertion into the incision 230. It may have a lip or ridge on the surface engaging the tissue to better hold it in place. The deflated tube-like structure is first properly positioned within the wound 230. Upon inflation, the tube under fluid pressure attempts to straighten itself out and, thus, opens the wound 230 (FIG. 19B) for easier access by the surgeon. As the retractor 232 presses on the edges 226 and 228 of the wound, it also compresses the tissue edges, giving a hemostatic effect. The retractor may be a bladder that pushes two metal or plastic pieces out to the sides, rather than pushing directly on the tissue itself. If the retractor is put vertically into a wound (see FIG. 19C) it expands the deep tissues. The depending legs 234 and 236 push outwardly as more fluid is admitted into the retractor, thus pushing the deep tissues apart. This is accomplished without making a correspondingly large opening in the skin.

Figure 20A:
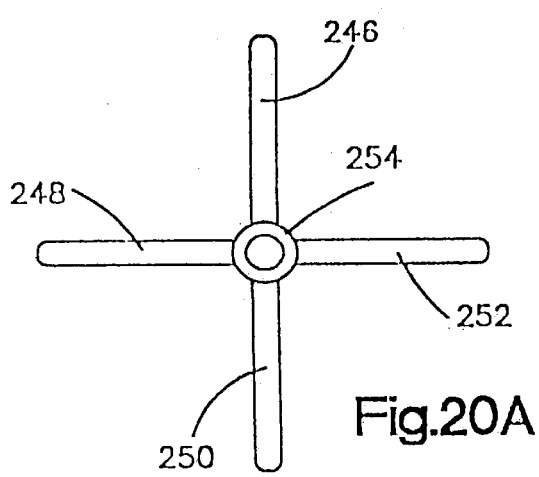
FIGS. 20A–D is a series of illustrating the provision of a plurality of separately inflatable bladders on one supporting structure.

As seen in FIG. 20A, a plurality of separately inflatable radially spaced bladders 246, 248, 250, 252, etc., can be located on one scope or cannula or rod 254. The bladders 246, 248, 250, 252 can be selectively inflated, possibly in a given sequence, to selectively retract tissue.

Figure 20B:
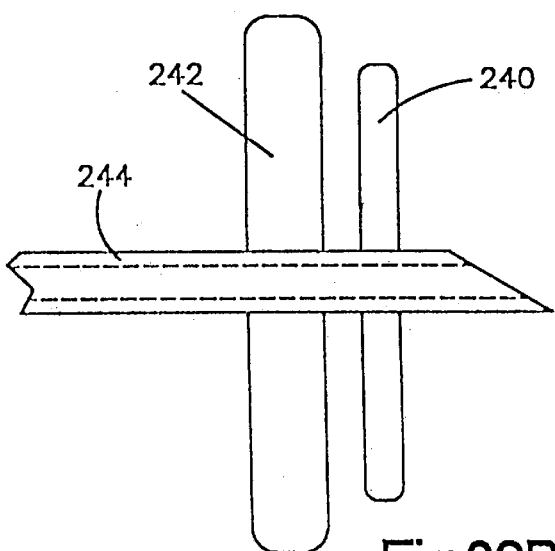
Figure 20C:
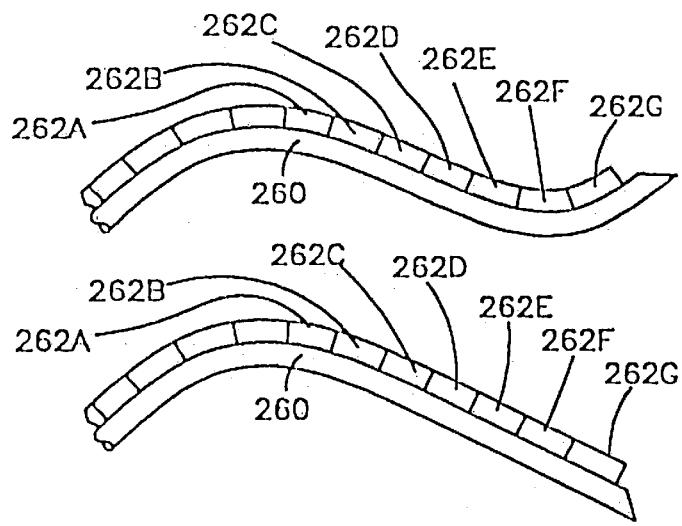
Figure 20D:
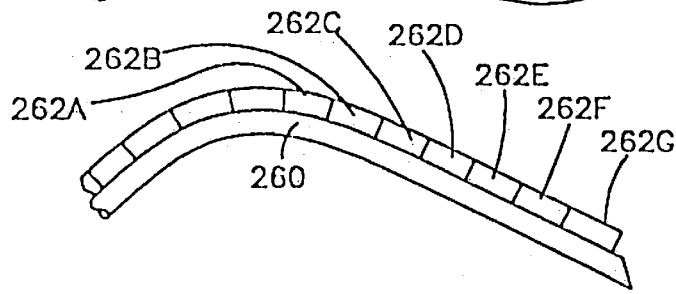

Alternatively, as seen in FIG. 20B a plurality of separately inflatable axially spaced bladders 240, 242, etc., can be located on one scope or cannula or rod 244. The bladders 240, 242 can be selectively inflated to selectively retract tissue. One particular use for such a capability is to push a tube or other device down the stomach without it curling back and up. FIG. 20C illustrates such a tube 260 having a plurality of bladders 262A through 262F that are deflated. When it is desired to selectively rigidify a portion of the tube 260, the bladders 262C through 262F are inflated (FIG. 20D), providing support for the tube at their corresponding axial locations and rigidifying the corresponding portion of the tube 260 as desired.

When a plurality of separately inflatable bladders are located on the same supporting device, suitable apparatus is provided for their inflation. Such apparatus may be, when only a few bladders are present, a simple mechanical valving apparatus. When more bladders are present, or more sophisticated or complex control thereof is desired, a microprocessor may be used to control the inflation. In such case, the control signals may be multiplexed down the structure via optical fiber or wire, for example.

Figure 21:
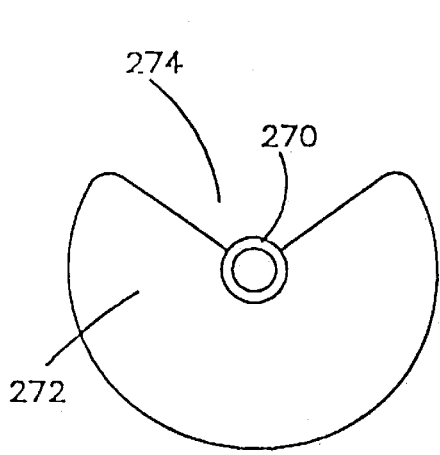
FIGS. 21 and 21A are schematic views illustrating the use of retractors of a certain shape to create a visualization and working space.
Figure 21A:
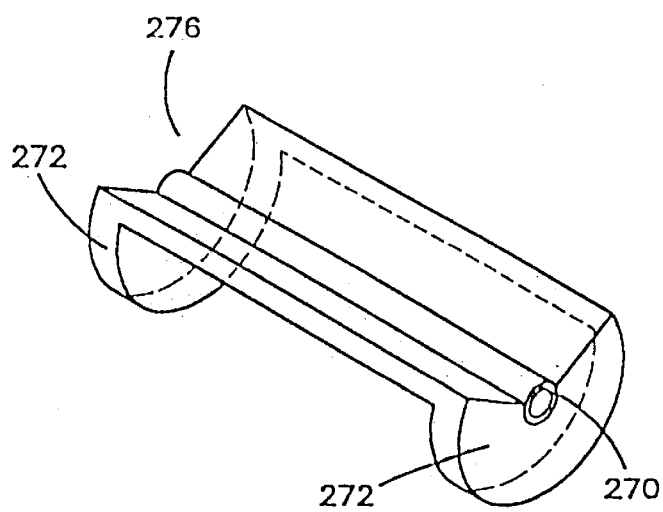

As further illustration of the variety of shapes of refractors which can be used, FIGS. 21 and 21A illustrate the provision of pie-shaped refractors which create a working space between the edges of the pie. The supporting structure carries a pie-shaped retractor 272 which, when inflated as shown, provides a space 274 for visualization and working. If two such refractors 272 are spaced axially as seen in FIG. 21A, an extended working and visualization area 272 is provided for the surgeon.

In the embodiment shown in FIG. 22, a bladder 280 is split at two locations 282, 284 so that when inflated it provides working and visualization areas between the lobes 286 and 288. Any number of such lobes may be provided, as seen in FIG. 22A showing a bladder 290 having four such lobes.

A surface of the retractor may be reflective, to allow the surgeon to see within the opening created by the retractor at different angles rather than merely straight in. The retractor 292 (FIG. 23) has a reflective surface or mirror 294 which enables visualization at an angle a which may be varied through inflation of the bladder 292 by various amounts. This is an especially appropriate use for the bellows type construction of the bladder as described above, wherein the surface of the bladder has a plurality of ridges 296. The retractor may thus be used to reflect light or a laser beam for visualization with a camera.

Another suitable use for the refractors of the present invention is in carpal tunnel surgery that can be otherwise quite difficult. The refractors are used to cup, move, and protect the nerves during the operation. FIG. 24 illustrates schematically a sectional view through a wrist 300 and showing the radius 302, ulna 304, median nerve 306, and tendons 308 and 310. A retractor 312 is inflatable radially outwardly in the directions indicated by the arrows 314, to push the tendons 310 in the direction indicated by the arrow 316 and away from the median nerve 306. Thus, space is created adjacent the tendons and median nerve, at a location axially from the retractor 312, for visualization and working. A second retractor 318 may be simultaneously used to create a longer working and visualization space 320, as seen in FIG. 24A.

From the foregoing description of preferred embodiments of the invention, those skilled in the art will perceive improvements, changes and modifications in the invention. Such improvements, changes and modifications within the skill of the art are intended to be covered by the appended claims.

What is claimed is:

1. A method of retracting soft tissue from a bone to create an operating space between the soft tissue and bone, the method comprising the steps of:
   providing a retractor comprising a relatively rigid member and an inflatable bladder mounted on the relatively rigid member, the inflatable bladder being formed of a substantially inelastic material having sufficient strength to withstand inflation pressures sufficient to enable the bladder to retract the soft tissue from the bone;
   making an incision in a body proximate a location of the bone and soft tissue, the incision providing access to the bone and soft tissue;
   introducing the relatively rigid member and deflated bladder into the incision and directing the deflated bladder with the relatively rigid member to the location of the soft tissue and bone;
   positioning the deflated bladder between the bone and soft tissue;
   inflating the bladder to retract the bone from the soft tissue to create the operating space; and
   inserting a surgical instrument, other than said retractor, into the operating space external to the bladder and prior to removing said retractor.

2. The method of claim 1 further comprising the step of performing a surgical procedure in the operating space created by inflating the bladder.

3. The method of claim 1 wherein the step of performing a surgical procedure in the operating space is performed while the bladder remains inflated.

4. The method of claim 1 further comprising the step of viewing the operating space with a scope.

5. The method of claim 1 wherein the bladder is inflated to a pressure in a range of about 100 to about 1000 mm Hg.

6. A method of retracting soft tissue from a bone to create an operating space between the soft tissue and bone, the method comprising the steps of:
   providing a retractor comprising a relatively rigid member and an inflatable bladder mounted on the relatively rigid member, the inflatable bladder being formed of a substantially inelastic material having sufficient strength to withstand inflation pressures sufficient to enable the bladder to retract the soft tissue from the bone;
   making an incision in a body proximate a location of the bone and soft tissue, the incision providing access to the bone and soft tissue;
   introducing the relatively rigid member and deflated bladder into the incision;
   advancing the relatively rigid member to position the deflated bladder between the bone and soft tissue;
   inflating the bladder to retract the bone from the soft tissue to create the operating space;
   inserting a surgical instrument, other than said retractor, into the operating space; and
   performing a surgical procedure in the operating space.

7. The method of claim 6 wherein the step of performing a surgical procedure in the operating space is performed while the bladder remains in the operating space.

8. The method of claim 7 wherein the step of performing a surgical procedure in the operating space is performed while the bladder remains inflated.

9. The method of claim 6 further comprising the step of viewing the operating space with a scope.

10. The method of claim 6 wherein the bladder is inflated to a pressure in a range of about 100 to about 1000 mm Hg.

11. A method of retracting soft tissue from a bone to create an operating space between the soft tissue and bone, the method comprising the steps of:
   providing a retractor comprising a relatively rigid member and an inflatable bladder mounted on the relatively rigid member, the inflatable bladder being formed of a substantially inelastic material having sufficient strength to withstand inflation pressures sufficient to enable the bladder to retract the soft tissue from the bone;
   making an incision in a body proximate a location of the bone and soft tissue, the incision providing access to the bone and soft tissue;
   introducing the relatively rigid member and deflated bladder into the incision;
   directing the relatively rigid member to the location of the soft tissue and bone to position the deflated bladder between the bone and soft tissue;
   inflating the bladder to retract the bone from the soft tissue to create the operating space; and
   inserting a surgical instrument into the operating space prior to removing the retractor.

12. The method of claim 11 further comprising the step of performing a surgical procedure in the operating space while the bladder remains in the operating space.

13. The method of claim 12 wherein the step of performing a surgical procedure in the operating space is performed while the bladder remains inflated.

14. The method of claim 11 further comprising the step of viewing the operating space with a scope.

15. The method of claim 11 wherein the bladder is inflated to a pressure in a range of about 100 to about 1000 mm Hg.

* * * * *